(12) United States Patent
Fischer et al.

(10) Patent No.: US 9,468,486 B2
(45) Date of Patent: Oct. 18, 2016

(54) METHOD FOR SELECTIVELY ELEVATING AND SEPARATING TISSUE LAYERS AND SURGICAL INSTRUMENT FOR PERFORMING THE METHOD

(75) Inventors: Klaus Fischer, Nagold (DE); Dan Maurice, Monument Beach, MA (US); John Day, Atlanta, GA (US); Markus Enderle, Tuebingen (DE)

(73) Assignee: ERBE ELEKTROMEDIZIN GMBH, Tuebingen (DE)

( * ) Notice: Subject to any disclaimer, the term of this patent is extended or adjusted under 35 U.S.C. 154(b) by 2074 days.

(21) Appl. No.: 12/285,072

(22) Filed: Sep. 29, 2008

(65) Prior Publication Data
US 2009/0157114 A1 Jun. 18, 2009

Related U.S. Application Data

(63) Continuation-in-part of application No. 11/918,251, filed as application No. PCT/EP2006/002328 on Mar. 14, 2006, now Pat. No. 8,979,836.

(30) Foreign Application Priority Data

Apr. 11, 2005 (DE) .................. 10 2005 016 602
May  4, 2005 (DE) .................. 10 2005 020 948
Aug. 16, 2005 (DE) .................. 10 2005 038 694

(51) Int. Cl.
A61B 18/18 (2006.01)
A61B 18/04 (2006.01)
A61B 17/00 (2006.01)
A61B 18/00 (2006.01)

(52) U.S. Cl.
CPC ....... *A61B 18/042* (2013.01); *A61B 17/00234* (2013.01); *A61B 2017/00269* (2013.01); *A61B 2018/00589* (2013.01)

(58) Field of Classification Search
CPC ............ A61B 18/14; A61B 17/32056; A61B 17/3203; A61M 5/30
USPC ............. 604/19, 32, 73, 264, 289, 290, 310; 606/37–50, 113
See application file for complete search history.

(56) References Cited

U.S. PATENT DOCUMENTS

| | | | | |
|---|---|---|---|---|
| 5,116,313 A * | 5/1992 | McGregor | ...................... | 604/70 |
| 5,158,561 A | 10/1992 | Rydell et al. | | |
| 5,254,117 A * | 10/1993 | Rigby et al. | ................... | 606/46 |
| 5,460,629 A * | 10/1995 | Shlain et al. | ................... | 606/46 |
| 5,505,729 A | 4/1996 | Rau et al. | | |

(Continued)

FOREIGN PATENT DOCUMENTS

| | | |
|---|---|---|
| DE | 2 333 720 | 1/1975 |
| DE | 36 42 077 | 6/1988 |

(Continued)

*Primary Examiner* — Emily Schmidt
(74) *Attorney, Agent, or Firm* — Blank Rome LLP

(57) ABSTRACT

A method for the selective elevation and separation of tissues comprised of multiple layers and a surgical instrument for performing the method. The method may be performed without the requirement of a solid mechanical device insertion or transection through the mucosal layer. In particular, the method and surgical instrument may be used for the selected separation and/or resection of selected portions of benign or malignant tissues (e.g. defining tissue planes, polyp elevation and removal, submucosal tissue tunneling, endoscopic mucosa resection, etc).

27 Claims, 11 Drawing Sheets

(56) References Cited

U.S. PATENT DOCUMENTS

| | | | |
|---|---|---|---|
| 5,620,414 A * | 4/1997 | Campbell, Jr. | 604/22 |
| 5,741,271 A * | 4/1998 | Nakao et al. | 606/114 |
| 6,007,546 A * | 12/1999 | Snow et al. | 606/113 |
| 6,010,512 A | 1/2000 | Chu et al. | |
| 6,123,665 A | 9/2000 | Kawano et al. | |
| 6,451,017 B1 * | 9/2002 | Moutafis et al. | 606/41 |
| 6,527,753 B2 | 3/2003 | Sekine et al. | |
| 6,689,126 B1 | 2/2004 | Farley et al. | |
| 6,752,799 B2 * | 6/2004 | Grund et al. | 604/508 |
| 2002/0055729 A1 * | 5/2002 | Goll | 604/507 |
| 2003/0009166 A1 | 1/2003 | Moutafis et al. | |
| 2003/0216724 A1 | 11/2003 | Jahns | |
| 2003/0233090 A1 | 12/2003 | Whayne | |
| 2006/0100614 A1 * | 5/2006 | Long | 606/27 |
| 2008/0055729 A1 * | 3/2008 | Li et al. | 359/601 |

FOREIGN PATENT DOCUMENTS

| | | |
|---|---|---|
| DE | 42 42 143 | 6/1994 |
| DE | 196 07 922 | 1/1998 |
| DE | 100 28 413 A1 | 9/2001 |
| EP | 0 280 972 A1 | 2/1988 |
| EP | 0 280 972 A1 | 9/1988 |
| EP | 0 555 549 A1 | 12/1992 |
| EP | 0 893 101 A2 | 1/1999 |
| JP | 05-212045 | 8/1993 |
| JP | 11-47154 A | 2/1999 |
| JP | 2000-262528 A | 9/2000 |
| JP | 2004-105367 A | 4/2004 |
| WO | WO 96/36381 | 11/1996 |
| WO | WO 03/096871 A2 | 11/2003 |

\* cited by examiner

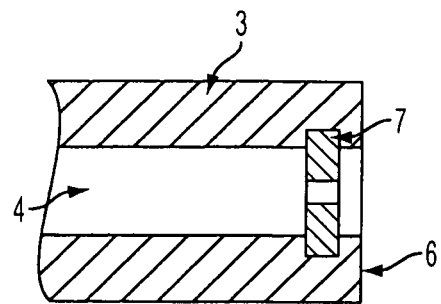
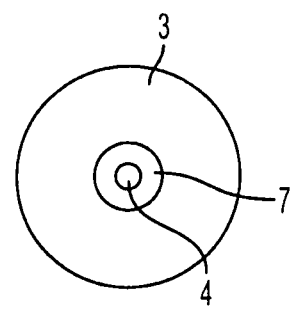
FIG. 1a     FIG. 1b
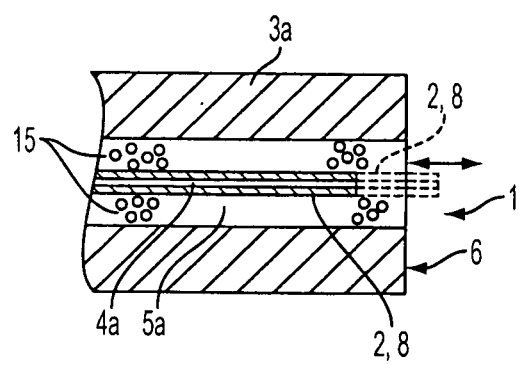
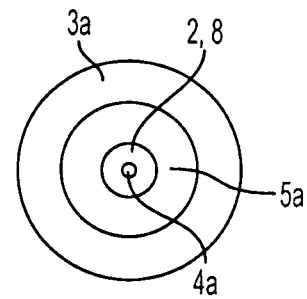
FIG. 2a     FIG. 2b

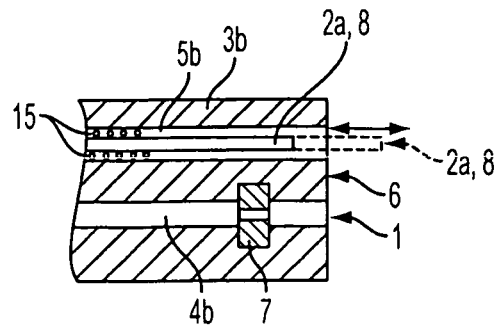
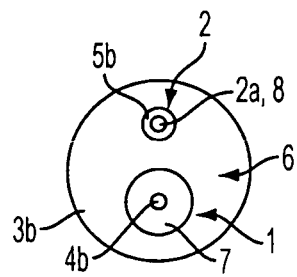
FIG. 3a  FIG. 3b
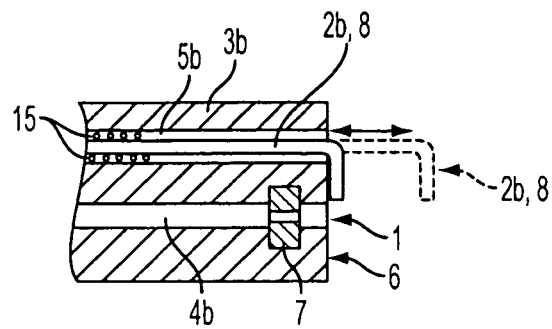
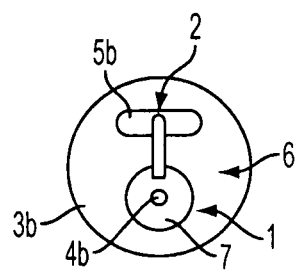
FIG. 4a  FIG. 4b
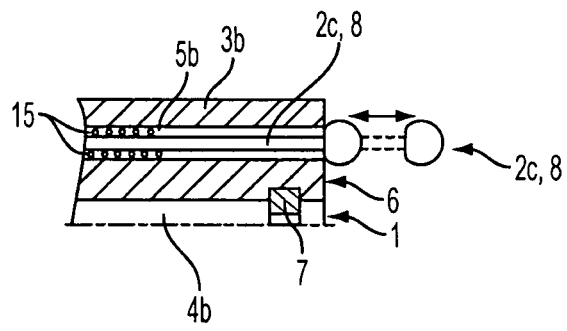
FIG. 5
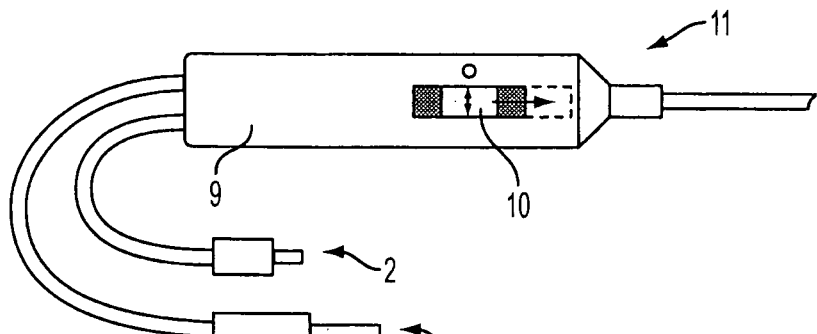
FIG. 6

METHOD FOR SELECTIVELY ELEVATING AND SEPARATING TISSUE LAYERS AND SURGICAL INSTRUMENT FOR PERFORMING THE METHOD

CROSS-REFERENCE TO RELATED APPLICATIONS

This application is a continuation-in-part of application Ser. No. 11/918,251, filed on Oct. 16, 2007, which is the U.S. national stage of International Application no. PCT/EP2006/002328, filed Mar. 14, 2006, the entire disclosures of both of which are incorporated by reference herein.

FIELD OF THE INVENTION

The invention relates to an improved method for the selective elevation and separation of tissues comprised of multiple layers using a tissue selective insertion method. In one embodiment, liquid is introduced without requiring a solid mechanical device insertion or transection through the mucosal layer and a surgical instrument for performing this method. In particular, the method and surgical instrument may be used for the tissue-selective separation and/or resection of selected portions of benign or malignant tissues (e.g., defining tissue planes, polyp elevation and removal, submucosal tissue tunneling, endoscopic mucosa resection, etc).

BACKGROUND OF THE INVENTION

During mucosa resection or removal of lesions on or in the wall of certain human and animal anatomy (e.g., gastrointestinal tract, bladder or peritoneal wall) by means of instruments (such as loops, or cutters with or without a cap), lasers, ultrasonic dissectors, etc., bleeding and perforation, for example, of the intestinal or gastric wall can occur. In order to manage these problems, liquid is typically injected under the mucosa into the submucosal layer, resulting in the creation of a "fluid pocket" before removal of lesions (e.g., polyps, adenomas, malignant or benign tumours, endometriosis implants). The primary purpose of this procedural step is to lift off or elevate the mucosal layer or another layer, and hence the lesion, from the muscularis or another layer of the wall. Penetration of the liquid under the mucosa layer causes the mucosa to be "loosened" from the deeper layers by forming a liquid cushion beneath the mucosa. This produces a safety separation or protective surgical margin from the deeper layers as well as providing a protective heat barrier from thermal energy sources.

Traditionally, the liquid injection procedure is done with a needle. These, conventional "needle injection" techniques for delivery of fluidic agents (in order to allow the subsequent removal of selected tissues) have several problems associated with them. One problem associated with these methods is that the user must rely on "tactile feel" and a constant delivery of fluid in order to precisely place the needle within the submucosal layer before additional liquid is injected under the mucosa via the needle. This process is relatively "unselective" and often results in complete perforation of the target tissue and whereas the fluid accumulates under the mucosal layer without integrating with the submucosal tissue matrix, the fluid escapes rapidly (e.g., in less than a few minutes). Additional problems associated with using conventional methods include difficulty in obtaining access to the delivery site (e.g., relative position of the device with respect to the tissue), necessity of repositioning the distal tip of the device in multiple locations, delivering the fluidic agent to the delivery site, accurately injecting the fluidic agent into the appropriate tissue layer or depth within the tissue, and problems maintaining fluid retention within the tissue, etc. In addition, injection of the fluidic agent becomes extremely difficult when the target tissues are moving or are pliable.

Conventionally, once the liquid cushion is formed beneath the mucosa, the mucosal resection is then performed using a snare or cap technique to achieve the operative goals. In the case of larger area tumors, however, a "piecemeal" technique is often employed. Alternatively and potentially more clinically desirable, the mucosa resection can be performed using an "enbloc technique" which is carried out with a flexible needle knife type of electrode. This technique for resection is extremely difficult. In particular, the difficulty of this type of intervention is that the injected liquid leaks out of the "fluid pocket" during the operation, causing the deeper layers to become thermally damaged by the needle knife. This thermal damage can in turn lead to perforation of hollow organs (e.g., intestine) or undesired thermal damage to other tissue layers or structures. In order to avoid perforation for instance, the instrument must be removed several times during the resection procedure and liquid must again be injected under the mucosa.

Accordingly, it is desirable to improve the targeted delivery of therapeutic, diagnostic, or fluidic agents via a tissue selective needle-less fluid introduction process that will facilitate the resection of undesired tissue with increased efficiency.

U.S. Pat. No. 6,752,799 (DE 19 607 922 C2) discloses a medical device and method for the endoscopic injection of a liquid underneath the mucosa. The device disclosed in this patent is spaced a distance away from the target tissue which allows for a thin fluid stream to substantially travel in "free flight" prior to contacting the tissue while the user holds the device at a specific angle. The fluid is introduced in such a thin stream that the hole created in the mucosa closes after itself without allowing an appreciable amount of fluid to escape. The device creates a "fluid pocket" under the mucosal layer. The initial fluid retention issue is addressed using a self sealing micro-hole, however, after the first incision is made, the fluid escapes rapidly. Therefore, continual re-introduction is still required as this device has not improved fluid retention within the tissue.

U.S. Pat. No. 6,126,633 discloses a medical device which is capable of approaching the target region in a safer and easier manner by bending and is used for submucosal needle injection. This addresses the relative position of the device with respect to the target tissue, but however neglects the other major obstacles associated with conventional needle designs.

U.S. Pat. No. 6,666,847 is directed toward providing an improved needle injection system that offers a surgeon easier needle extension and retraction.

Alternative solutions to the problems of bleeding and intestinal perforation are also being tested wherein liquids of different viscosities are used; however, these liquids still leak out of the mucosa. These attempts still do not offer a satisfactory solution because the escape of the liquid out of the submucosa is only slowed, but is not prevented.

Each of these patents discloses devices for submucosal needle injection, however, they fail to address all or the majority of the problems associated with this technically challenging and high risk procedure. For example, these patents do not address the difficulties of "manually" finding the appropriate tissue plane without the risk of complete colonic transection or perforation with a needle device (layer thicknesses range from 0.5 mm to 1.5 mm), the limitations on the device approach to the target tissue, and problems with maintaining fluid retention within the tissue.

It is therefore desired to have a surgical instrument that facilitates the selective introduction of a fluid into tissue layers to allow for elevation and separation of tissue layers. In particular, it is desired to have a surgical instrument that allows the elevation and separation without the requirement for a solid mechanical device insertion or transection through the mucosal layer. In addition, improvements in fluid retention within the target tissue, a device which can approach the tissue at any angle, and/or resection of selected tissues, which will thereby help prevent and avoid damage to surrounding tissues during subsequent procedures are also desired.

SUMMARY OF THE INVENTION

Embodiments of the invention provide a surgical instrument that includes a device for feeding in at least one liquid, in particular for introduction of a liquid resulting in selective tissue elevation or separation, and/or dissection. The device may also include a device for high frequency surgery, wherein the device for high frequency surgery may be combined with the device for feeding in the at least one liquid, in order to achieve uniform handling. A multifunction device may thereby be achieved, which combines the advantages of water jet surgery (including introduction of liquid for selective tissue elevation or separation and/or dissection by means of liquid) with the advantages of high frequency surgery. The surgical instrument according to the disclosed embodiments makes it possible to selectively introduce a liquid under the mucosal layer into the submucosa to thereby selectively lift and/or separate selected tissue layers.

Liquid may be introduced under the mucosal layer in a needleless fashion, without the need for manually finding the appropriate tissue plane and without requiring a solid mechanical device insertion or transection through the mucosal layer. Additionally, the mucosal layer may also be coagulated, cut or removed by the water jet when operated at a suitable pressure, so that three functions can be fulfilled by the surgical instrument in accordance with the invention: selective introduction of the liquid into the submucosa layer, coagulation and resection (cutting) of the mucosal layer.

In another embodiment, resection of the mucosal layer is performed using a device for high frequency surgery without the aid of the liquid. For uniform handling purposes, the various arrangements of the device for feeding in the at least one liquid and/or a high frequency electrode are provided in a single probe to offer a solution for combining the device for feeding in the at least one liquid (e.g., nozzle) and the device for high frequency surgery (e.g., high frequency electrode).

The high frequency electrode may take several forms. For example, the high frequency electrode may be any type known in the art, such as a needle, hook, needle with an insulated tip, disk, snare or a snare with an insulated tip, by which means the field of application of the device is widened. Any type of snare (i.e., symmetrical or asymmetric snares, snares with or without insulated tips, snares with different shapes or diameters) can be used. The design of a high frequency needle electrode (preferably a retractable micro needle) can be used as a delivery mechanism of a suitable fluid pressure stream in order to deliver at least one fluid into the submucosal layer and alter the tissue properties of said layer, as is described in more detail herein.

In any of the embodiments, the surgical instrument may further comprise a handle which also has a switch, in particular a sliding switch, for switching on the device for high frequency surgery and is connectable to a separate switch, in particular a foot switch, for activating the device for high frequency surgery. Two spatially separate switches must thereby be actuated, so that the device for high frequency surgery is switched on by the sliding switch and then activated by actuating the separate foot switch. It is thereby ensured that the device for high frequency surgery is not accidentally activated during a procedure. A separate foot switch can be adapted both for activating the device for high frequency surgery and for activating the feeding-in of the at least one liquid, so that by means of the separate foot switch, both the feeding-in of the liquid and the activation of the high frequency electrode can be actuated.

The probe may be comprised of a plastic hose, which results in a particularly simple and economical solution for designing a flexible probe. Alternatively, the probe may be comprised of a flexible metal tube, which is insulated on the outer periphery. By means of the metal inner core, the probe diameter can be significantly reduced without a severe loss of flexibility. Those skilled in the art can substitute a variety of suitable materials and activation devices, which can be used without deviating from the true scope and spirit of the disclosed invention.

The surgical instrument according to the disclosed embodiments allow for the selective elevation of the mucosa by introduction of a liquid under the mucosa at any angle, separation of the mucosal layer from an underlying tissue layer and fluid diffusion/penetration into the submucosal tissue matrix (which allows for improved fluid retention within the selected layer). With the aid of a single surgical device, changing instruments during the operation in order to re-inject liquid during resection is no longer required. Rather, when using the surgical instrument according to the invention, if the liquid begins to slowly diffuse or leak out of the submucosal tissue matrix, the device is simply switched over from cutting mode to liquid introduction mode and additional liquid is introduced into the submucosal tissue matrix.

By selectively targeting the submucosal tissue layer (comprised primarily of collagen) with a liquid delivered at a suitable pressure, the normal tissue properties of the submucosal tissue matrix can be altered, thereby addressing one of the major problems associated with the conventional "needle injection" technique, fluid retention within the tissue. Operating times can therefore be significantly reduced because the instruments do not have to be removed and the fluid retention of the tissue has been significantly improved. Another advantage of the surgical instrument according to the disclosed embodiments is that the function of introducing liquid under the mucosal layer for separation and selective tissue elevation of the tissue layers may be implemented without insertion of a needle or other mechanical instrument into the tissue. This is made possible by the tissue selective properties of the method and device. Advantages of this "needleless" tissue elevation method (as compared to other mechanically invasive methods) include automatically defining the appropriate tissue plane, improved fluid retention within the tissue, reliability, ease of use, faster and higher elevation and more predictability with respect to the introduction of the liquid.

BRIEF DESCRIPTION OF THE DRAWINGS

These and other features and advantages of the disclosed embodiments will be better understood by referencing the following detailed description and when considered in conjunction with the following figures.

FIG. 1a is a longitudinal cross-sectional view of the distal end of a probe for liquid introduction in accordance with an exemplary embodiment.

FIG. 1b is a transverse cross-sectional view of the probe of FIG. 1a.

FIG. 2a is a longitudinal cross-sectional view of the distal end of a probe with a combined high frequency needle and channel for liquid introduction, according to an exemplary embodiment.

FIG. 2b is a transverse cross-sectional view of the probe of FIG. 2a.

FIG. 3a is a longitudinal cross-sectional view of the distal end of a probe with a high frequency needle, according to another exemplary embodiment.

FIG. 3b is a transverse cross-sectional view of the probe of FIG. 3a.

FIG. 4a is a longitudinal cross-sectional view of the distal end of a probe with a high frequency hook, according to another exemplary embodiment.

FIG. 4b is a transverse cross-sectional view of the probe of FIG. 4a.

FIG. 5 is a longitudinal cross-sectional view of the distal end of a probe with a high frequency needle with an insulated tip, according to another exemplary embodiment.

FIG. 6 is a side view of a handle including a liquid connection and a high frequency connection.

DETAILED DESCRIPTION OF THE INVENTION

Figure 7:
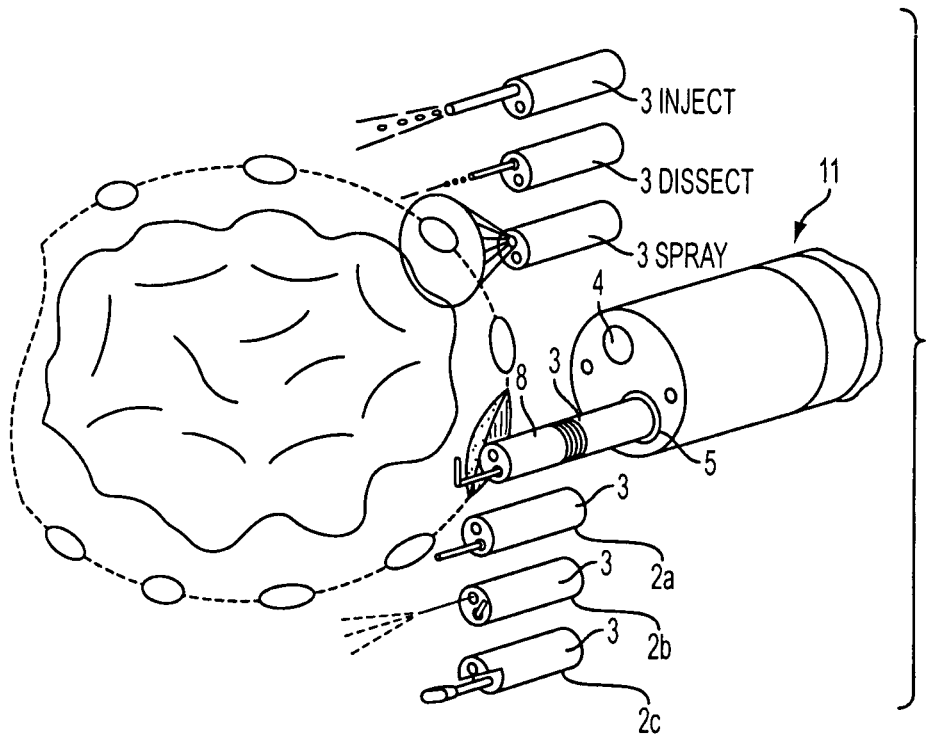
FIG. 7 is a diagram showing the sequence of an endoscopic intervention using a surgical instrument according to the disclosed embodiments.

In one embodiment of the invention, a catheter device is provided and used for the delivery of a fluidic, therapeutic or diagnostic agent under a suitable pressure (selected on the basis of targeting a selected tissue layer) in order to selectively elevate, separate, and/or resect selected portions of tissues. As shown in FIGS. 1a and 1b, the distal end 6 of probe 3 comprises a channel 4 for feeding through at least one liquid through nozzle 7 at a suitable pressure. The suitable pressure can be changed according to the desired task. For selectively elevating and separating tissues, a certain target pressure is desired; for coagulating small vessels, a different target pressure may be desired; and for resecting or cutting selected tissues, a different target pressure may be desired. Probe 3 is preferably flexible in nature and can be comprised of a variety of different suitable materials. For example, the flexible probe 3 may be constructed from, nylon, PEEK, polyimide, stainless steel, PTFE, etc.

FIGS. 2a and 2b show the distal end 6 of a probe 3a according to another exemplary embodiment. The probe 3a includes a single channel 5a through which a device 2 for high frequency surgery (e.g., high frequency electrode 8) can be fed. The device 2 can also take the form of a retractable micro needle that may be used to penetrate or transect tissue prior to fluid introduction in accordance with the invention. A rarefied gas 15, for example argon gas (AR), may also be introduced into channel 5a through conventional means, for example, a handle or port (not shown). The introduction of this gas supports a standard electrosurgical function, argon plasma coagulation, commonly used in clinical practice. At least one liquid, e.g. NaCl solution, can be fed through a channel 4a within the device 2 for high frequency surgery. Channel 4a is therefore part of the device 1 for feeding in at least one liquid. A supply container for the liquid and a pump arrangement (discussed below) by which the liquid is forced through channel 4a under suitable pressure are also provided and connectable to the device 1.

FIGS. 3a and 3b show the distal end 6 of a probe 3b according to another exemplary embodiment. The probe 3b has two channels 4b, 5b. Channel 5b can also accept the introduction of a rarefied gas 15 (e.g., AR) through conventional means. Nozzle 7 is firmly arranged in one of the channels 4b. At least one liquid, in particular a NaCl solution, can be fed through channel 4b. Channel 4b is therefore part of the device 1 for feeding in at least one liquid. A supply container for the liquid and a pump arrangement by which the liquid is forced through the channel 4b under a suitable pressure are also provided.

Probe 3b also includes a device 2 for high frequency surgery. This device 2 for high frequency surgery, for example, for cutting, coagulation, and/or dissection, comprises a high frequency electrode 8, which is provided in the other channel 5b of the probe 3b. The two channels 4b, 5b are arranged substantially parallel to one another. It should be noted that this embodiment of the invention is not restricted to two channels and can comprise additional channels, in particular three or four channels, wherein different functions can be assigned to each of the channels. For example, two separate channels could be provided for the fluid introduction mode and the dissection mode, in addition to the channel provided for the high frequency electrode 8.

Depending on the field of application, the high frequency electrode 8 may comprise a high frequency needle 2a (FIG. 3a), a high frequency hook 2b or spatula (FIG. 4a) arranged in a twist-proof manner, a high frequency needle with insulated tip 2c, in particular a ceramic tip (FIG. 5) or a disk (not shown). The device 1 shown in FIG. 3a may also comprise a handle 9, shown in FIG. 6. The handle 9 has a connection for the device 2 for high frequency surgery, which can be connected to a high frequency unit (not shown). The handle 9 also has at least one liquid connection of the device 1 for feeding in the at least one liquid, which can be linked to a water jet surgery unit (not shown) or to any other type of pump system which may provide the desired amount of pressure. The two connection lines are fed through the handle 9 and, for example, inserted into endoscope 11 shown in FIG. 7. The handle 9 also may have a switch 10, in particular a sliding switch, the actuation of which allows the high frequency electrode 8 to be positioned and switched on. For positioning, the high frequency electrode 8 is moved out of the probe 3a, 3b, as indicated by the double arrow and the dotted representation of the electrode 8 in FIGS. 2a, 3a, 4a and 5. Devices for optical monitoring of the intervention, such as light guides (not shown), may also be provided in the endoscope 11 (FIG. 7).

The device 1 for feeding in the at least one liquid (i.e., the device for water jet surgery), can be switched from the fluid introduction mode to the dissection mode, and vice versa, by a suitable control system. Activation of the high frequency electrode 8 may be carried out with a foot switch (not shown), by which means unintentional actuation of the electrode 8 is reliably avoided. Activation of the water jet can be carried out with the same foot switch. Conventional switching mechanisms may be use in whole or in part by those skilled in the art.

The pump arrangement by which the liquid is forced through channel 4a shown in FIGS. 1a, 1b, 2a and 2b, for high frequency and water jet surgery or channel 4b shown in FIGS. 3a, 3b, 4a, 4b and 5 can be any device which is suitable for creating the required pressures. For example, the ErbeJet and ErbeJet2 manufactured and sold by ERBE Elektromedizin GmbH or a disposable syringe connected via a detachable or permanent pressure-tight connection (e.g., luer lock or other) to a flexible endocapillary which is connected to a pump unit or force amplifier may be used. The force amplifier (e.g., large lever, balloon dilatation syringe or pump unit) creates the required pressures for selective tissue separation and elevation and resultant tissue altering characteristics.

The surgical instrument and the endoscope 11 shown in FIG. 7 may be used in accordance with certain aspects of the invention. As shown in FIG. 7, the water jet surgery function of the surgical instrument is activated and a fluid introduction jet is created using either channel 4a (FIGS. 1a, 1b, 2a and 2b) or a combination of the channel 4b and the nozzle 7 of the probe 3b (FIGS. 3a, 3b, 4a, 4b and 5) so that a liquid, particularly a NaCl solution, is introduced through the mucosa into the submucosal tissue matrix. This forms a long lasting liquid cushion under the mucosa so that the mucosa is lifted off the Muscularis propria. In the next step, the surgical instrument is switched from fluid introduction mode to dissection mode, wherein the pressure of the water jet is increased so that the mucosa can be resected. Additionally, the pressure of the water jet can be further modified to coagulate small vessels.

In comparison and when the instrument is then switched from the water jet function to the high frequency surgical function and the electrode 8 is positioned, the submucosa is separated, during which time the coagulating effect of the electrode 8 comes into play.

In a needleless hydrodissection, separation or elevation mode, a fluid is transported selectively under suitable pressure into the submucosa or another desired layer of the selected tissue. The pressure is chosen so that the fluid selectively penetrates and integrates only with the desired tissue layer. Referring to FIGS. 1a and 1b, the distal end of the device 1 for feeding in at least one liquid is placed firmly on the desired hydrodissection site or target tissue without the requirement of the endocapillary piercing the mucosa. Alternatively, in the case of previous mucosal insult (i.e., thermal or mechanical breach), the distal end firmly touches the mucosa or mucosal defect (thermal or mechanical), without the need for re-positioning the device. The fluid is transferred via a suitable pressure and selectively diffuses, integrates or penetrates into the submucosal tissue layer matrix.

By applying a suitable pressure while touching the tissue with the end of the probe, the fluid accumulates precisely in the desired layer. The collagen rich submucosal tissue matrix layer is thereby altered while the fibrin-rich muscularis layer is automatically preserved via the principles of our tissue-selective hydrodissection technique whereby fibrin-rich structures have the ability to deflect a given fluid delivered at a suitable pressure. Therefore, the fluid accumulates and evenly diffuses precisely within the targeted submucosal layer and is not transferred into an underlying fibrin-rich muscularis layer. Further, the needleless hydrodissection may be used either alone or in combination with other instruments (e.g., snare wire, biopsy forceps, cutting loop, laser fibre, etc).

Needleless, tissue-selective transport of fluid into the submucosa tissue matrix by means of a flexible endocapillary requires, in most cases, a pressure of 5 to 70 bar, by way of example. This allows for a faster, potentially safer, more reproducible, predictable, reliable, durable and often a larger degree of tissue plane separation, elevation, or hydrodissection.

Accordingly, by using the disclosed embodiments it is possible to lift the mucosa sufficiently off the Muscularis propria and excise it without the gastric or intestinal wall being damaged, while using only a single instrument. Specifically, it is possible to re-introduce liquid into the submucosa if the submucosa begins to lose too much liquid during the course of an extended operation, without changing devices, in order to keep the mucosa adequately spaced from the gastric or intestinal wall.

Figure 8:
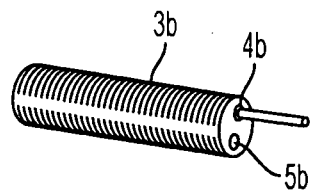
FIG. 8 is a perspective view of an exemplary embodiment wherein the device is operated in a fluid introduction mode.
Figure 9:
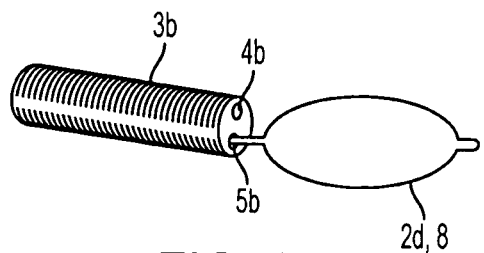
FIG. 9 is a perspective view of an exemplary embodiment wherein the device is operated in a high frequency mode.
Figure 10:
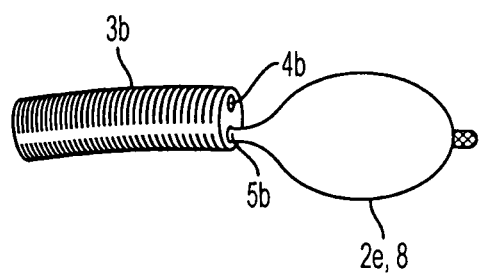
FIG. 10 is a perspective view of an exemplary embodiment wherein the probe includes a high frequency snare with an insulated tip.
Figure 11:
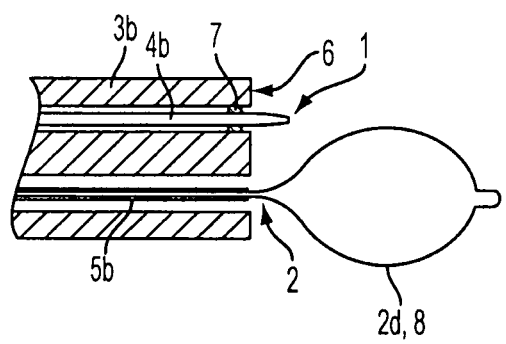
FIG. 11 is a longitudinal cross-sectional view of a probe with a high frequency snare without an insulated tip, according to an exemplary embodiment.

Further exemplary embodiments of the invention are shown in FIGS. 8 to 11. These embodiments are similar to the embodiments discussed with reference to FIGS. 3a, 3b, 4a, 4b and 5. The embodiments of FIGS. 8 to 10 are particularly suited toward polypectomy procedures and comprise a probe 3b with two channels 4b, 5b, of which one channel 4b serves for the introduction of a liquid jet and the other channel 5b serves to accommodate a high frequency snare 2d (without an insulated tip (FIGS. 9, 11)) or 2e (with an insulated tip (FIG. 10)). The two channels are integrated into a single probe 3b for uniform operation. The uniform operation of the fluid introduction device and the high frequency electrode 8 (e.g., high frequency snare 2d or 2e) can be achieved with the embodiment according to FIGS. 8 to 11 in a similar manner as that described with reference to the other embodiments.

The design of the probe according to FIGS. 8 to 11 substantially corresponds to the above described design of the probe according to the previously described exemplary embodiments. A nozzle 7, through which the liquid jet for fluid introduction or dissection emerges, is arranged in one of the two channels, e.g., channel 4b. A high frequency snare is arranged in the other of the two channels, e.g., channel 5b and can be drawn into or pushed out of the channel 5b. All types of snares in different forms and diameters and snares 2e with an insulated tip (FIG. 10) and snares 2d without an insulated tip (FIGS. 9, 11) are suitable. Furthermore, symmetrical or asymmetric and/or rotatable or non-rotatable snares can be used.

The design of a high frequency electrode as a snare with or without an insulated tip is particularly suitable, for e.g., a polypectomy. It has previously been problematic, that under certain circumstances, a polyp was not sufficiently spaced from the muscularis layer and could not be lifted off. The cutting height, therefore, was a matter of judgment for the surgeon. The surgeon was required to balance between removing a sufficient amount of the polyp such that no "risky" material (which later could regenerate) is left in the body while maintaining a sufficient distance away from the muscularis layer so as not to endanger the tissue of the intestinal wall (i.e., risk of perforation). The combination of a high frequency snare and a device for feeding in at least one liquid, as in several disclosed embodiments of the invention, enables the selective introduction of a liquid under the polyp, so that it is sufficiently spaced from the muscularis layer. The polyp can then be excised or resected with less risk and the tissue of the intestinal wall or underlying tissue layer will not be damaged or incur less damage.

The functioning of the probes 3b according to the exemplary embodiments as per FIGS. 8 to 11 substantially corresponds to the functioning of the exemplary embodiments described above, wherein, in the fluid introduction mode, a liquid jet, preferably 0.9% NaCl solution, is introduced into the submucosa under the polyps, so that it is sufficiently spaced from the submucosa. The polyp is then resected or excised by means of the snare 2d, 2e.

While FIGS. 3a-11 illustrate various alternative embodiments of the device 2 for high frequency surgery implemented in a device having two channels, each of these types of devices 2 for high frequency surgery may also be implemented in an instrument having a single channel, in a similar manner as that illustrated in FIGS. 1a, 1b, 2a and 2b.

Figure 12A:
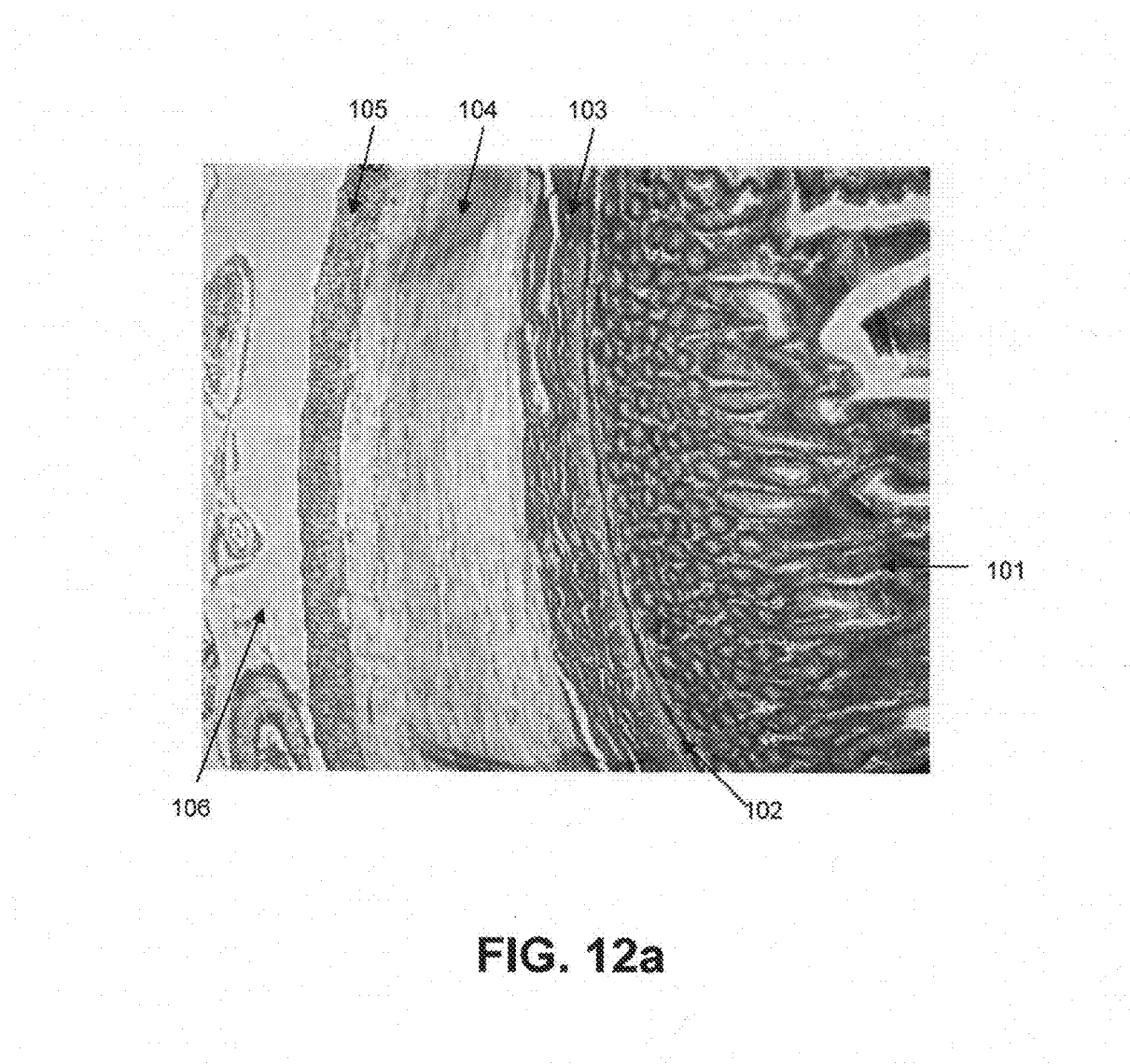
FIG. 12a is a cross-sectional histological photograph of the gastrointestinal tract showing the basic tissue layers.
Figure 12B:
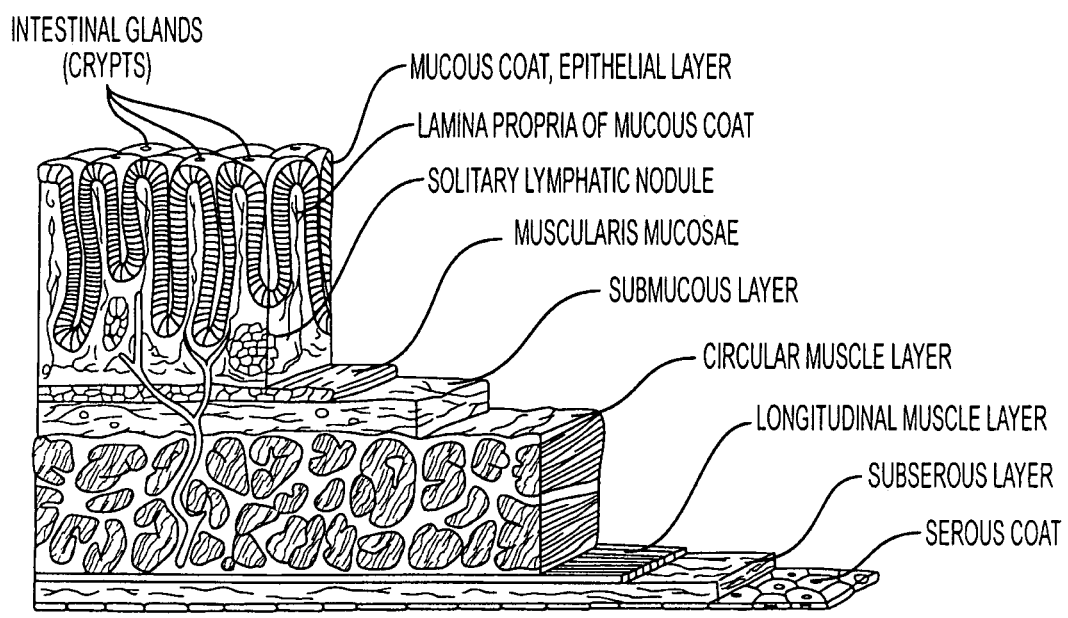
FIG. 12b is a cross-sectional illustration of the gastrointestinal tract depicting the basic tissue layers.

A histological cross-sectional photograph of the gastrointestinal (GI) tract, clearly showing the basic layers, is provided as FIG. 12a. The glandular mucosa 101 (to the right) is quite dark because of all the epithelial and connective tissue nuclei it contains. A thin strip of pink marks the muscularis mucosae 102. Next comes a very dark pink submucosa 103, which is mainly dense collagen fibers. Further left are two, paler pink layers of the muscularis externa: a wide band of inner circular smooth muscle 104 and a narrower band of outer longitudinal smooth muscle 105. Furthest left is the serosa 106, which can be recognized due to its "finished" edge of mesothelium. This particular photograph is likely near the mesenteric attachment because there is so much adipose tissue and some fairly large blood vessels within the serosa 106. FIG. 12b is a cross-sectional illustration of the gastrointestinal tract depicting the basic tissue layers. FIGS. 12a and 12b are provided to allow for a clear understanding of the tissue anatomy as well as help further understand the altered tissue characteristics of the targeted tissue layer after the tissue selective needleless fluid introduction device and method have been applied (see FIG. 13b).

Figure 13A:
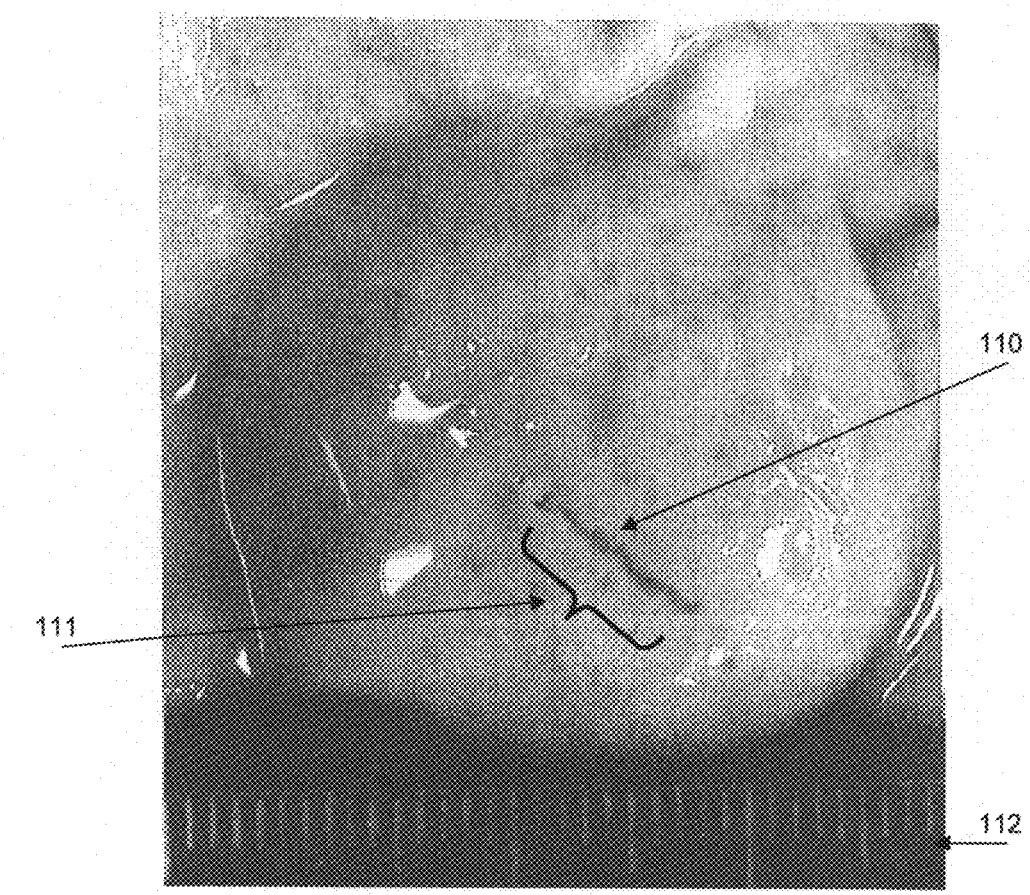
FIG. 13a is a macroscopic view of the needleless elevation technique of the disclosed embodiments used in an in-vivo environment.
Figure 13B:
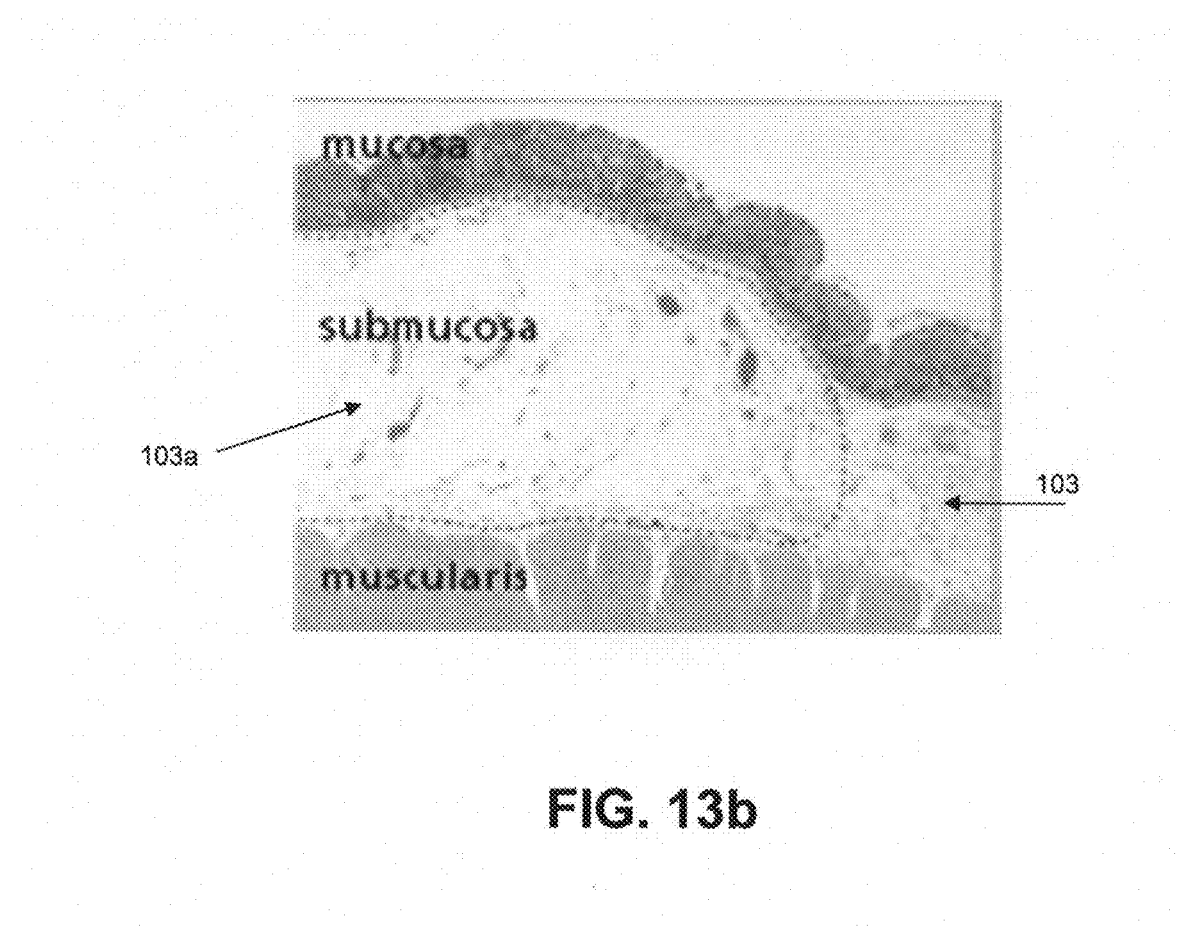
FIG. 13b is a cross-sectional histological photograph of the gastrointestinal tract depicting the fluid diffusion into the submucosal tissue matrix.

FIG. 13a is a macroscopic view of the needleless elevation technique used in an in-vivo environment. The mucosal defect (hole) 110 caused by the selective needleless elevation technique can clearly be seen, having an overall length 111 (centimeter measurement device 112 provides a frame of reference). The overall length 111 of the mucosal defect shown in FIG. 13a is in excess of 1 centimeter, however, in accordance with the disclosed embodiments, the saline does not leak out of the tissue in a rapid fashion after the fluid integration into the submucosal tissue matrix. FIG. 13b is a cross-sectional histological view of the gastrointestinal tract depicting the fluid diffusion (edema or swelling, fluid integration, 103a) into (penetration) the submucosal tissue matrix 103. The inventor's extensive tissue research has supported this "tissue altering" needleless elevation technique, which has not previously been seen or reported in clinical reports. By altering the submucosal tissue matrix, fluid retention is greatly improved without worrying about the size of the mucosal breach.

Figure 14:
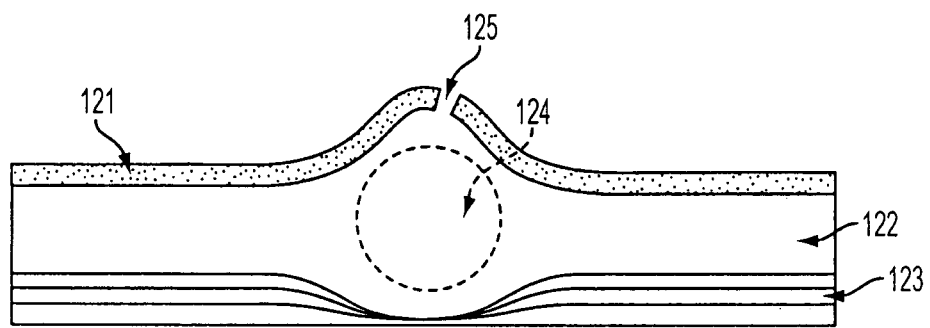
FIG. 14 is a cross-sectional illustration of the gastrointestinal tract depicting the "fluid pocket" produced by a standard needle injection device.

By comparison, FIG. 14 is a cross-sectional illustration of the gastrointestinal tract depicting the "fluid pocket" produced by a standard needle injection device. The mucosal layer 121, submucosal layer 122 and muscularis layer 123 can be seen in FIG. 14. The "fluid pocket" 124 created by the needle injection method and the needle tract 125 associated with the initial insertion can also be seen. When the fluid is "unselectively" delivered to the target tissue by this conventional technique, fluid escapes around the injection site 125 and continues to do so very rapidly. The "fluid pocket" 124 is mostly devoid of any collagen and primarily consists of the fluid delivered.

Figure 15A:
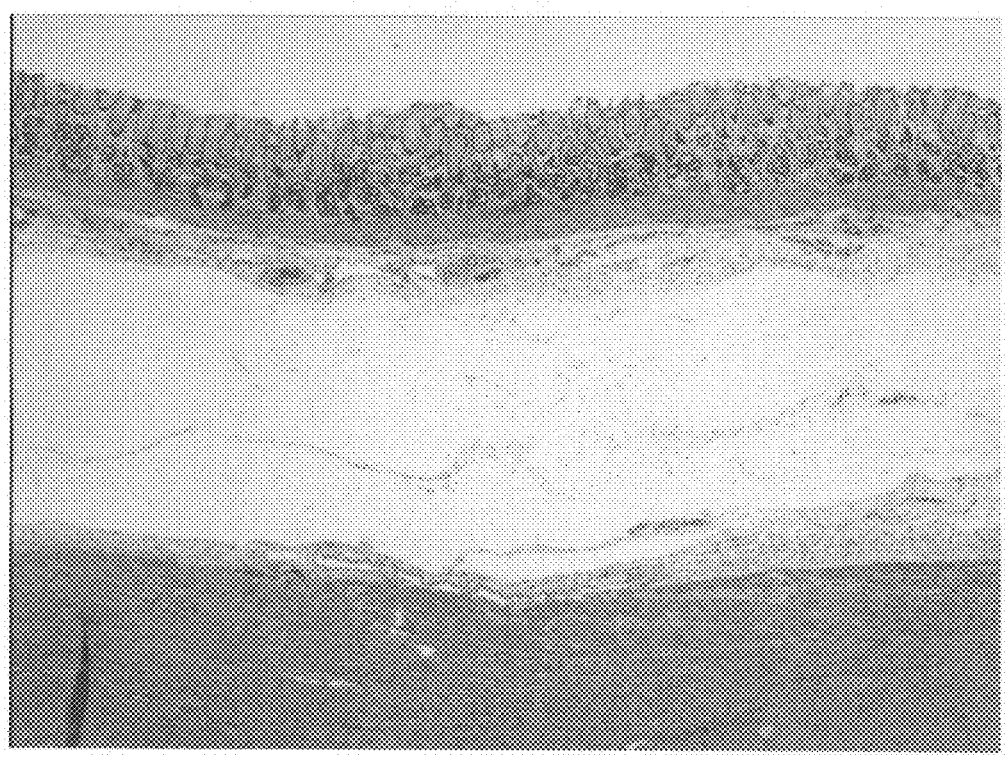
FIG. 15a is a cross-sectional histological photograph of the gastrointestinal tract depicting the fluid diffusion throughout the submucosal tissue matrix, when using disclosed embodiments.
Figure 15B:
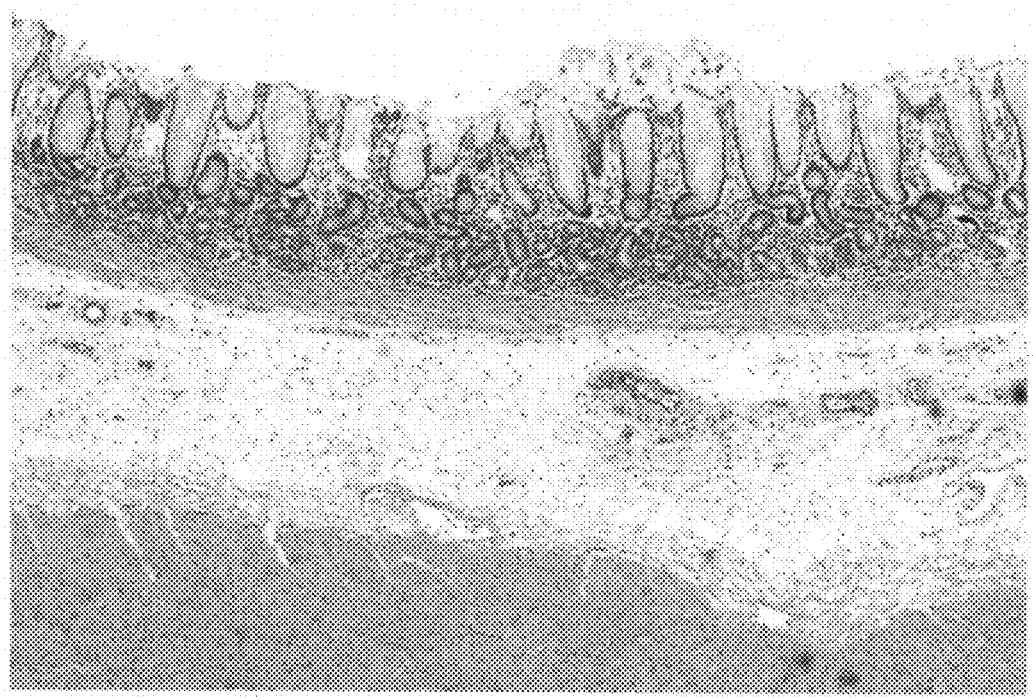
FIG. 15b is a cross-sectional histological photograph of the gastrointestinal tract depicting a lack of fluid diffusion throughout the submucosal tissue matrix, when not using disclosed embodiments.

Referring to FIGS. 15a and 15b a further comparison of the disclosed embodiments with known methods of liquid introduction can be seen. FIG. 15a is a cross-sectional histological view of the gastrointestinal tract depicting fluid diffusion throughout the submucosal tissue matrix, in accordance with disclosed embodiments. FIG. 15b is a cross-sectional histological photograph of the gastrointestinal tract depicting a submucosa without the fluid diffusion created by using the disclosed embodiments. When viewed in comparison with FIG. 15b, it can clearly be seen in FIG. 15a that the disclosed embodiments provide liquid diffusion throughout the submucosa, thereby allowing for the improved liquid retention in the submucosa.

It should be noted that while various exemplary embodiments have been described with respect to their use in endoscopic mucosal resection of the gastrointestinal tract, the invention also has applicability in any implementation in which tissue-selective needleless separation, elevation and/or resection of tissue layers is desired such as, for example, polypectomy; endoscopic submucosal dissection (ESD) of large superficial tumours of the esophagus, stomach and colon; removal of tumours of the bladder wall; endometriosis implants on the peritoneal wall; or separation of organs (hydrodissection) using a non-mechanical means (e.g., separation of the gall bladder from the liver capsule using the principle of needleless hydrodissection of fibrin-rich structures).

The disclosed embodiments have been described herein in considerable detail in order to provide those skilled in the art with a thorough understanding of the novel principles of the invention, method of application, and the various uses thereof without limitation. It is understood by those skilled in the art that the invention can be carried out by various modifications without undue experimentation and deviating from the true scope and spirit of the invention.

What is claimed as new and desired to be protected by Letters Patent of the United States is:

1. A surgical method comprising:
providing a device for feeding in at least one liquid;
selectively transferring the liquid into a specified layer within a target tissue, wherein the liquid is transferred using a pressure suitable for selective liquid transfer, the pressure being at a level such that the liquid accumulates within the specified layer within the target tissue and does not pierce or transfer into an underlying layer, thereby separating or elevating a portion of the target tissue; and
resecting the separated or elevated portion of the target tissue, wherein the resection is performed using at least one liquid delivered by the device for feeding in at least one liquid, wherein the liquid used for resection is delivered at a pressure suitable for resection.

2. The method of claim 1, wherein a distal end of the device for feeding in the at least one liquid does not mechanically transect or pierce a target tissue during the transferring.

3. The method of claim 2, further comprising placing the distal end of the device for feeding in at least one liquid on the target tissue before transferring the liquid.

4. The method of claim 2, further comprising placing the distal end of the device for feeding in at least one liquid near a target tissue, such that the distal end is directed at but does not touch the target tissue, before transferring the liquid.

5. The method of claim 1, wherein the pressure suitable for selective liquid transfer is configured such that the liquid integrates with and alters the physical tissue characteristics of the specified layer within the target tissue.

6. The method of claim 5, wherein the liquid is retained within the specified layer in the target tissue for a period of time which allows for resection of the separated or elevated portion without requiring reintroduction of liquid into the specified layer.

7. The method of claim 5, wherein the liquid is retained within the specified layer in the target tissue for a period of time which allows for coagulation of the separated or elevated portion without requiring reintroduction of liquid into the specified layer.

8. The method of claim 1, wherein the underlying layer is a fibrin-rich muscularis layer.

9. The method of claim 1, wherein the pressure suitable for selective liquid transfer is between about 10 bar and about 70 bar.

10. The method of claim 1, wherein the at least one liquid is a biocompatible solution.

11. The method of claim 10, wherein the at least one liquid is a NaCl solution.

12. The method of claim 1, wherein the separated or elevated portion of the target tissue is benign.

13. The method of claim 1, wherein the separated or elevated portion of the target tissue is malignant.

14. The method of claim 1, wherein the resection is performed using a high frequency surgical cutting device.

15. The method of claim 1, wherein the resection is performed using high frequency surgical cutting of the separated or elevated portion of the target tissue combined with coagulation of the separated or elevated portion of the target tissue.

16. The method of claim 1, further comprising coagulating the separated or elevated portion of the target tissue.

17. The method of claim 16, wherein the coagulation is performed using a high frequency surgical coagulation device.

18. A surgical method comprising:
providing a device for feeding in at least one liquid; and
selectively transferring the liquid into a specified layer within a target tissue; and
resecting the separated or elevated portion of the target tissue,
wherein the liquid is transferred into the specified layer using a pressure suitable for selective liquid transfer, the pressure being at a level such that the liquid accumulates within the specified layer within the target tissue and does not pierce or transfer into an underlying layer, thereby separating or elevating a portion of the target tissue,
wherein a distal end of the device for feeding in the at least one liquid does not mechanically transect or pierce a target tissue during the transferring, and
wherein the resection is performed using at least one liquid delivered by the device for feeding in at least one liquid, wherein the liquid used for resection is delivered at a pressure suitable for resection.

19. A surgical method comprising:
providing a device for feeding in at least one liquid; and
selectively transferring the liquid into a specified layer within a target tissue,
wherein the liquid is transferred using a pressure suitable for selective liquid transfer, the pressure being at a level such that the liquid accumulates within the specified layer within the target tissue and does not pierce or transfer into an underlying layer, thereby separating or elevating a portion of the target tissue,
wherein the pressure suitable for selective liquid transfer is configured such that the liquid integrates with and alters the physical tissue characteristics of the specified layer within the target tissue, and
wherein the liquid is retained within the specified layer in the target tissue for a period of time which allows for coagulation of the separated or elevated portion without requiring reintroduction of liquid into the specified layer.

20. A surgical instrument comprising:
a device for feeding in at least one liquid and for providing the liquid at a suitable pressure such that the liquid may be selectively transferred into a selected tissue layer such that the liquid accumulates within, integrates with and alters the physical characteristics of the selected tissue layer, wherein the suitable pressure is between about 10 bar and about 70 bar; and
a device for high frequency surgery,
wherein the surgical instrument comprises at least one channel comprising the device for feeding in at least one liquid and at least one additional channel for the device for high frequency surgery.

21. The surgical instrument of claim 20, wherein the suitable pressure is at a level to allow selective liquid transfer such that the liquid may be transferred into the selected tissue layer without mechanically piercing an overlying layer with the device for feeding in the at least one liquid and without transferring liquid into an underlying layer.

22. The surgical instrument of claim 21, wherein the overlying layer is a mucosal layer and the selected tissue layer into which the liquid is selectively transferred is a submucosal layer and the underlying layer into which liquid is not transferred is a fibrin-rich muscularis layer.

23. The surgical instrument of claim 20, wherein the device for high frequency surgery is a high frequency needle.

24. The surgical instrument of claim 23, where the high frequency needle includes an insulated tip.

25. The surgical instrument of claim 20, wherein the device for high frequency surgery is a high frequency hook.

26. The surgical instrument of claim 20, wherein the device for high frequency surgery is a high frequency spatula.

27. The surgical instrument of claim 20, wherein the device for high frequency surgery is a snare wire.

* * * * *